(12) United States Patent
Rozot et al.

(10) Patent No.: US 7,396,525 B2
(45) Date of Patent: Jul. 8, 2008

(54) CARE/MAKEUP COMPOSITIONS COMPRISING A 2-ALKYLIDENEAMINOOXYACETAMIDE COMPOUND FOR STIMULATING THE GROWTH OF THE HAIR OR EYELASHES AND/OR SLOWING LOSS THEREOF

(75) Inventors: Roger Rozot, Lagny/Marne (FR); Christophe Boulle, Lagny/Marne (FR); Maria Dalko, Gif S/Yvette (FR)

(73) Assignee: L'Oreal, Paris (FR)

( * ) Notice: Subject to any disclaimer, the term of this patent is extended or adjusted under 35 U.S.C. 154(b) by 127 days.

(21) Appl. No.: 11/181,910

(22) Filed: Jul. 15, 2005

(65) Prior Publication Data
US 2006/0026775 A1   Feb. 9, 2006

Related U.S. Application Data

(63) Continuation of application No. PCT/IB2004/000291, filed on Jan. 12, 2004.

(60) Provisional application No. 60/441,733, filed on Jan. 23, 2003.

(30) Foreign Application Priority Data
Jan. 15, 2003   (FR) .................................. 03 50001

(51) Int. Cl.
*A61C 5/00*   (2006.01)
(52) U.S. Cl. ...................... 424/70.1; 424/401; 424/70.7
(58) Field of Classification Search ........................ None
See application file for complete search history.

(56) References Cited

U.S. PATENT DOCUMENTS

5,750,558 A   5/1998   Brooks et al.
5,840,758 A   11/1998  Brooks et al.

FOREIGN PATENT DOCUMENTS

| EP | 0 321 274 A1 | 6/1989 |
| EP | 0 427 445 A1 | 5/1991 |
| GB | 1447580 | 8/1976 |
| WO | WO 00/33834 A1 | 6/2000 |

OTHER PUBLICATIONS

"The science of Hair Care" By Charles Zviak, Chapter 17, pp. 451-467 (1986).*
Buzas et al., "Synthese et proprietes pharmacologique d'esters et ethers d'oximes", Chimie Therapeutique, 1972, pp. 140-142, No. 2.
International Search Report corresponding to PCT/IB 2004/000291, issued on Dec 2, 2004, 3 pages.

* cited by examiner

*Primary Examiner*—Jyothsna Venkat
(74) *Attorney, Agent, or Firm*—Buchanan, Ingersoll & Rooney, PC

(57) ABSTRACT

A regime/regimen (and compositions therefor) for inducing and/or stimulating the growth of keratinous fibers and/or slowing the loss and/or increasing the density thereof, notably human hair and/or eyelashes, entails administering to a mammalian subject in need of such treatment, for such period of time as required to elicit the desired effect, a thus effective amount of at least one 2-alkylideneaminooxyacetamide compound having the formula (I):

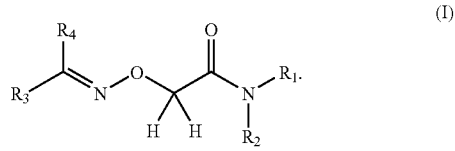

(I)

4 Claims, No Drawings

CARE/MAKEUP COMPOSITIONS COMPRISING A 2-ALKYLIDENEAMINOOXYACETAMIDE COMPOUND FOR STIMULATING THE GROWTH OF THE HAIR OR EYELASHES AND/OR SLOWING LOSS THEREOF

CROSS-REFERENCE TO PRIORITY/PCT/PROVISIONAL APPLICATIONS

This application claims priority under 35 U.S.C. § 119 of FR 03/50001, filed Jan. 15, 2003, and of provisional application Ser. No. 60/441,733, filed Jan. 23, 2003, and is a continuation of PCT/IB 2004/000291, filed Jan. 12, 2004 and designating the United States (published in the English language on Aug. 19, 2004 as WO 2004/069213 A2); each hereby expressly incorporated by reference and each assigned to the assignee hereof.

BACKGROUND OF THE INVENTION

1. Technical Field of the Invention

The present invention relates to compositions for caring for or making up keratinous fibers, in particular human keratinous fibers, comprising an effective amount of an oxyacetamide compound and more particularly of a 2-alkylideneaminooxyacetamide compound, which compositions are useful to induce and/or stimulate the growth of keratinous fibers and/or to slow down their loss. It additionally relates to a cosmetic treatment regime or regimen suited to stimulate the growth of keratinous fibers and/or to slow down their loss.

The human keratinous fibers to which the present invention relates are in particular the hair, eyebrows, eyelashes, beard hairs, moustache hairs and pubic hairs. More especially, this invention relates to human hair and/or eyelashes.

In particular, the present invention relates to compositions for caring for or making up the hair or eyelashes, comprising an effective amount of an oxyacetamide compound, suited to increase their density and/or to improve their appearance.

2. Description of Background and/or Related and/or Prior Art

The growth of the hair and its renewal are mainly determined by the activity of the hair follicles and of their matrix environment. Their activity is cyclical and essentially comprises three phases, namely the anagen phase, the catagen phase and the telogen phase.

The anagen phase (active or growth phase), which lasts several years and during which the hair lengthens, is succeeded by a very short and transitory catagen phase, which lasts a few weeks. During this phase, the hair undergoes a change, the follicle atrophies and its implantation in the skin appears less and less deep.

The terminal phase or telogen phase, which lasts several months, corresponds to a resting phase of the follicle and the hair finishes by falling out. At the end of this resting period, a new follicle is regenerated there and another cycle recommences.

The hair is therefore continuously renewed and, of the approximately 150,000 individual hairs which make up the hair, approximately 10% are at rest and will be replaced in a few months.

The natural loss of the hair can be estimated, on average, at a few hundred hairs per day for a normal physiological state. This constant physical renewal process undergoes a natural change during the course of aging; the hairs become finer and their cycles shorter.

In addition, various causes can result in a significant, temporary or definitive, hair loss. The hair can be lost or detrimentally affected during recovery from pregnancy (post partum), during conditions of undernourishment or of dietary imbalances or during conditions of asthenia or of hormonal dysfunctioning, as may be the case during the course of or during recovery from the menopause. Hair can also be lost or detrimentally affected in connection with seasonal phenomena.

It may also be a matter of alopecia, which is essentially due to a disturbance of hair renewal which results, first, in an acceleration in the frequency of the cycles to the detriment of the quality of the hair and then of its amount. The successive growth cycles result in hair which is increasingly fine and increasingly short and which is gradually converted to an unpigmented down. Areas are preferentially affected, in particular the temples or the front of the head in men, and, in women, a diffuse alopecia of the vertex is observed.

The term "alopecia" also covers a whole family of conditions of the hair follicle having, as a final consequence, partial or general permanent hair loss. It is a matter more particularly of androgenic alopecia. In a significant number of cases, early hair loss takes place in genetically predisposed subjects; it is then a matter of androchronogenetic alopecia. This form of alopecia affects men in particular.

Furthermore, it is known that certain factors, such as hormonal imbalance, physiological stress or malnutrition, can accentuate the phenomenon.

In some dermatosis conditions of the scalp with an inflammatory nature, such as, for example, psoriasis or seborrhoeic dermatitis, hair loss can be greatly increased or can result in highly disrupted cycles of the follicles.

Need has long existed for many years, in the cosmetic or pharmaceutical industry, for compositions which make it possible to eliminate or reduce alopecia and in particular to induce or stimulate hair growth or to decrease hair loss.

From this viewpoint, a large number of compositions comprising very diverse active principles, such as, for example, 2,4-diamino-6-piperidinopyrimidine 3-oxide or "minoxidil", disclosed in U.S. Pat. Nos. 4,139,619 and 4,596,812, or its numerous derivatives, such as those disclosed, for example, in EP-0,353,123, EP-0,356,271, EP-0,408,442, EP-0,522,964, EP-0,420,707, EP-0,459,890 and EP-0,519,819, have already been proposed.

Clinical studies have demonstrated that $PGF_{2\alpha}$ analogues have the property of bringing about the growth of body hairs and eyelashes in man and animals (Murray A. and Johnstone M. D., 1997, *Am. J. Opht.*, 124(4), 544-547). In man, tests carried out on the scalp have shown that a prostaglandin $E_2$ analogue (viprostol) has the property of increasing hair density (Roenigk H. H., 1988, *Clinic Dermatol.*, 6(4), 119-121).

Furthermore, WO 98/33497 discloses pharmaceutical compositions comprising prostaglandins or prostaglandin derivatives intended to combat hair loss in man. Prostaglandins of the $A_2$, $F_{2\alpha}$ and $E_2$ type are mentioned as preferred.

However, prostaglandins are molecules with a very short biological half-life which act autocrinally or paracrinally, this reflecting the local and labile nature of the metabolism of prostaglandins (Narumiya S. et al., 1999, *Physiol. Rev.*, 79(4), 1193-1226).

It thus appears important, to maintain and/or increase hair density in man, to retain the endogenous reserves of $PGF_{2\alpha}$ and of $PGE_2$ in the various compartments of the hair follicle or of its immediate cutaneous environment.

A solution which provides good results is the use of compounds which are inhibitors of lipoxygenase and/or inducers of cyclooxygenase for the purpose of promoting hair growth;

one hypothesis is that the use of such compounds directs the metabolism of the fatty acids towards the endogenous synthesis of prostaglandins in preference to other routes.

However, to further improve the results, it would be desirable to be able to prolong the activity of the prostaglandins involved in the growth and the preservation of the individual living hair.

Furthermore, it is well known that the programs of differentiation of the keratinocytes of the epidermis and of the hair follicle are clearly different. Thus, it is known that the keratins of the hair shaft represent a family (Langbein et al., 2001, *J. Biol. Chem.*, 276, 35123-35132) distinct from that expressed in the epidermis, that differentiation markers such as keratins $K_1$ and $K_{10}$ are not expressed in the hair follicle and in particular in the outer sheath (Lenoir et al., 1988, *Dev. Biol.*, 130, 610-620), that trichohyalin (O'Guin et al., 1992, *J. Invest. Dermatol.*, 98, 24-32) and keratin K6irs (Porter et al., 2001, *Br. J. Dermatol.*, 145, 558-568) are expressed in the hair follicle, in particular in the inner sheath, but not in the epidermis, and that cyclooxygenase type 1, while it is expressed in the epidermis, is not expressed in the keratinocytes of the hair follicle but in the dermal papilla (Michelet et al., 1997, *J. Invest. Dermatol.*, 108, 205-209).

SUMMARY OF THE INVENTION

Applicants have now demonstrated that an enzyme specifically involved in the decomposition of these prostaglandins is present in the dermal papilla of the individual hair, which is a determining compartment for the life of the individual hair. This is because Applicants have now proved the presence of type 1 15-hydroxyprostaglandin dehydrogenase (abbreviated to 15-PGDH) therein. In addition, it has now been shown that the inhibition of type 1 15-PGDH has a beneficial effect on hair growth.

The present invention thus relates to compositions for hair care or treatment comprising at least one specific inhibitor of type 1 15-hydroxyprostaglandin dehydrogenase and a physiologically acceptable medium.

Type 1 15-PGDH is a key enzyme in the deactivation of prostaglandins, in particular of $PGF_{2\alpha}$ and of $PGE_2$, which are important mediators of the growth and survival of the individual hair. It corresponds to the EC 1.1.1.141 classification and is NAD+-dependent. It has been isolated from pig kidney; its inhibition by a thyroid hormone, triiodothyronine, at doses much greater than physiological doses has in particular been observed. Type 2 15-PGDH is, for its part, NADP-dependent.

However, provision had never been made to use a type 1 15-PGDH inhibitor for maintaining and/or increasing the density of human keratinous fibers and in particular of human hair and/or for reducing the heterogeneity in the diameters of keratinous fibers and in particular of head hairs in man. Increasing the density of keratinous fibers and in particular hair density means increasing the number or the diameter of keratinous fibers and in particular of head hairs per cm$^2$ of skin or of scalp.

Thus, it has now been found that certain 2-alkylideneaminooxyacetamide compounds and in particular certain thiophene- or furanaminooxyacetamides, which may or may not be salified, surprisingly elicit a favorable activity in improving the density of keratinous fibers and in particular hair fibers. Moreover, it has also been found that these compounds are inhibitors of 15-hydroxyprostaglandin dehydrogenase.

Accordingly, the present invention features compositions for caring for or making up keratinous fibers, in particular human keratinous fibers, comprising, in a physiologically acceptable medium, an effective amount of a 2-alkylideneaminooxyacetamide compound of formula (I) or of one of its salts:

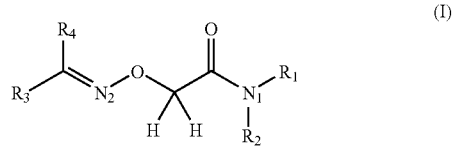

in which:
a) $R_1$ and $R_2$ are selected independently from:
  1) saturated or unsaturated and linear or branched $C_1$-$C_{20}$ alkyl radicals optionally substituted by at least one substituent $T_1$ selected from:
    halogens,
    $CF_3$, CN, OR, SR, NRR', NRC(=NR')NR"R', COR, CSR, COOR, CONRR', NRCOR', NRCONR'R", $SO_2$NRR', $NRSO_2R'$, $SO_2R$ or SiRR'R" groups,
    saturated or unsaturated ring members, of 4 to 7 atoms, optionally comprising at least one heteroatom to form a heterocycle Hy, it being possible for these rings optionally to be fused, to comprise a carbonyl or thiocarbonyl functional group and/or to be substituted by at least one substituent $T_2$,
  2) saturated or unsaturated ring members, of 4 to 7 atoms, optionally comprising at least one heteroatom to form a heterocycle Hy, it being possible for these rings optionally to be fused, to comprise a carbonyl or thiocarbonyl functional group and/or to be substituted by at least one substituent $T_3$ selected from:
    halogens,
    $CF_3$, CN, OR, SR, NRR', NRC(=NR')NR"R', COR, CSR, COOR, CONRR', NRCOR', NRCONR'R", $SO_2$NRR', $NRSO_2R'$, $SO_2R$ or SiRR'R" groups,
    saturated or unsaturated and linear or branched $C_1$-$C_{20}$ alkyl radicals optionally substituted by at least one substituent $T_1$,
    saturated or unsaturated ring members, of 4 to 7 atoms, optionally comprising at least one heteroatom to form a heterocycle Hy, it being possible for these rings optionally to be fused, to comprise a carbonyl or thiocarbonyl functional group and/or to be substituted by at least one substituent $T_2$,
    provided that, in the case where $R_1$ and $R_2$ are both heterocycles Hy, at least one heterocycle is connected to the nitrogen $N_1$ of the formula (I) via a carbon;
  3) CN, C(=NR)R', C(=NR)NR'R", COR, CSR, COOR or CONRR' groups;
  4) $R_1$ can also be a hydrogen atom or an $SO_2R$ or $SO_2NRR'$ group;
  5) $R_1$ and $R_2$ can also form a heterocycle Hy optionally substituted by at least one substituent $T_2$ and optionally fused to an aryl radical or to a saturated or unsaturated carbonaceous ring of 4 to 7 atoms and which can comprise a carbonyl or thiocarbonyl functional group, or fused to another heterocycle Hy;
b) $R_3$ and $R_4$ are selected independently from:
  1) linear or branched $C_1$-$C_{20}$ alkyl radicals or carbonaceous rings of 4 to 7 atoms and which can comprise a carbonyl or thiocarbonyl functional group, these alkyl groups or these rings being saturated or unsaturated and optionally substituted by at least one substituent $T_4$ selected from:

halogens,

CF$_3$, CN, OR, SR, NRR', NRC(=NR')NR"R', COR, CSR, COOR, CONRR', NRCOR', NRCONR'R", SO$_2$NRR', NRSO$_2$R', SO$_2$R or SiRR'R" groups, aryl radicals or heterocycles Hy, these radicals and heterocycles optionally being substituted by at least one substituent T$_2$ and optionally being fused to an aryl radical or to a saturated or unsaturated carbonaceous ring of 4 to 7 atoms and which can comprise a carbonyl or thiocarbonyl functional group, or these radicals and heterocycles optionally being fused to another heterocycle Hy;

2) aryl radicals and heterocycles Hy, these aryl radicals and these heterocycles optionally being fused to an aryl radical or to a saturated or unsaturated carbonaceous ring of 4 to 7 atoms and which can comprise a carbonyl or thiocarbonyl functional group, or these aryl radicals and these heterocycles optionally being fused to a heterocycle Hy, these aryl radicals, this carbonaceous ring or these heterocycles Hy optionally being substituted by at least one substituent T$_3$;

3) CF$_3$, CN, OR, SR, NRR', NRC(=NR')NR"R', COR, CSR, COOR, CH$_2$COOR, CONRR', NRCOR', NRCONR'R", SO$_2$NRR', NRSO$_2$R', SO$_2$R or SiRR'R" groups;

4) R$_3$ and R$_4$ can also be a hydrogen atom;

c) R, R', R" and R', which may be identical or different, are each one of the following groups:

a hydrogen, a saturated or unsaturated and linear or branched C$_1$-C$_{20}$ alkyl radical optionally substituted by at least one substituent T$_2$, saturated or unsaturated ring members, of 4 to 7 atoms, optionally comprising at least one heteroatom to form a heterocycle Hy, it being possible for these rings optionally to be fused, to comprise a carbonyl or thiocarbonyl functional group and/or to be substituted by at least one substituent T$_2$;

d) T$_2$ represents:

a saturated or unsaturated and linear or branched C$_1$-C$_{20}$ alkyl radical, a halogen, a group selected from CN, CF$_3$, OR$_5$, SR$_5$, NR$_5$R$_6$, NR$_5$C(=NR$_6$)NR$_7$R$_8$, COR$_5$, CSR$_5$, COOR$_5$, CH$_2$COOR$_5$, CONR$_5$R$_6$, NR$_5$COR$_6$, NR$_5$CONR$_6$R$_7$, SO$_2$NR$_5$R$_6$, NRSO$_2$R$_5$, SO$_2$R$_5$ or SiR$_5$R$_6$R$_7$, in which R$_5$, R$_6$, R$_7$ and R$_8$, which may be identical or different, are each hydrogen or a saturated or unsaturated and linear or branched C$_1$-C$_{20}$ alkyl radical, an aryl radical or a heterocycle Hy optionally fused to an aryl radical or to a saturated or unsaturated carbonaceous ring of 4 to 7 atoms, or fused to another heterocycle Hy;

e) Hy represents a saturated or unsaturated heterocycle of 4 to 7 atoms and which can comprise from 1 to 4 heteroatoms selected from N, O and S and/or which can comprise a carbonyl or thiocarbonyl functional group.

The invention also applies to the keratinous fibers of non-human mammals (dogs, horses, sheep or cats, for example).

The present invention also features the cosmetic use of at least one oxyacetamide of formula (I) or of one of its salts in a cosmetic composition for caring for and/or making up human keratinous fibers in order to induce and/or stimulate their growth, to slow down their loss and/or to increase their density and to the use of at least one compound of formula (I) or of one of its salts in the preparation of a composition for caring for or treating human keratinous fibers suited to induce and/or stimulate the growth of the fibers and/or to slow down their loss and/or to increase their density.

The human keratinous fibers to which the invention applies are in particular the hair, eyebrows, eyelashes, beard hairs, moustache hairs and pubic hairs. More especially, the invention applies to human hair and/or eyelashes.

Consquently, this invention also features compositions for caring for or making up keratinous fibers, in particular a hair care or mascara composition, for topical application comprising a physiologically acceptable medium and an effective amount of at least one compound of formula (I) or of one of its salts, as described above.

The present invention also features the use, in particular cosmetic use, of at least one 2-alkylideneaminooxyacetamide compound of formula (I) or of one of its salts, as defined above, as active agent for inducing and/or stimulating the growth of keratinous fibers, in particular human keratinous fibers, and/or slowing down their loss and/or increasing their density.

This invention also features the formulation of at least one 2-alkylideneaminooxyacetamide compound of formula (I) or of one of its salts into a cosmetic composition for human hair care in order to reduce hair loss and/or to increase hair density. The present invention also features the use of at least one 2-alkylideneaminooxyacetamide compound of formula (I) or of one of its salts in the preparation of a human hair composition suited to induce and/or stimulate the growth of the hair and/or to slow down hair loss and/or to increase hair density.

In particular, the present invention features the formulation of at least one 2-alkylideneaminooxyacetamide compound of formula (I) or of one of its salts into a cosmetic composition for human hair care or into a human hair composition for treating or suited to treat alopecia of natural origin and in particular androgenic or androchronogenetic alopecia. Thus, such a composition makes it possible to maintain the hair in good condition and/or to combat natural hair loss and more especially that of men.

The present also features the formulation of at least one oxyacetamide compound of formula (I) or of one of its salts into a cosmetic composition for caring for and/or for making up human eyelashes, for inducing and/or stimulating the growth of the eyelashes and/or increasing their density and the use of at least one compound of formula (I) or of one of its salts in the preparation of a composition for caring for and/or treating human eyelashes intended to induce and/or stimulate the growth of the eyelashes and/or to increase their density. Such a composition thus makes it possible to keep the eyelashes in good condition and/or to improve their condition and/or their appearance.

This invention also features the use of at least one 2-alkylideneaminooxyacetamide compound of formula (I) or of one of its salts as inhibitor of type 11 5-hydroxyprostaglandin dehydrogenase of the human skin. And this invention also features the use of at least one 2-alkylideneaminooxyacetamide compound of formula (I) or of one of its salts in the manufacture of a composition suited to treat disorders related to type 1 15-hydroxyprostaglandin dehydrogenase, in particular in human being.

Too, the present invention features a regime or regimen for the cosmetic treatment of keratinous fibers (in particular hair or eyelashes) and/or of the skin from where the said fibers emerge, including the scalp and eyelids, to stimulate the growth of human keratinous fibers and/or slow down their loss, comprising topically applying, to the keratinous fibers and/or the skin from where the said fibers emerge, a cosmetic composition comprising an effective amount of at least one compound of formula (I) or of one of its salts, in leaving this composition in contact with the said fibers and/or the said skin, and optionally in rinsing the said fibers and/or the said skin.

This treatment process exhibits the characteristics of a cosmetic process in so far as it makes it possible to improve the attractiveness of the keratinous fibers (in particular hair and eyelashes) by giving them greater vigor and an improved appearance. In addition, it can be used daily for several months without a medical prescription.

More especially, the present invention features a regime or regimen for the cosmetic care of human hair and/or the human scalp for the purpose of improving their condition and/or their appearance, comprising topically applying, to the hair and/or the scalp, a cosmetic composition comprising an effective amount of at least one compound of formula (I) or one of its salts, in leaving this composition in contact with the hair and/or the scalp and optionally in rinsing the hair and/or the scalp.

This invention also features a regime or regimen for the cosmetic care of and/or for making up human eyelashes for the purpose of improving their condition and/or their appearance, comprising topically applying, to human eyelashes and/or eyelids, a mascara composition comprising at least one compound of formula (I) or one of its salts and in leaving this composition in contact with the eyelashes and/or eyelids. This mascara composition can be applied alone or as an undercoat of a conventional pigmented mascara and can be removed like a conventional pigmented mascara.

This invention also features compositions for caring for or making up keratinous fibers comprising, in a physiologically acceptable medium, in particular a cosmetic medium, at least one compound of formula (I) or one of its salts and at least one additional active principle which promotes the regrowth of human keratinous fibers and/or which limits their loss selected from aminexil, FP receptor agonists and vasodilators and selected more especially from aminexil, minoxidil, latanoprost, butaprost and travoprost.

This invention also features the cosmetic use of at least one compound of formula (I) or of one of its salts in a cosmetic composition as active agent for preserving the amount and/or the activity of prostaglandins in the hair follicle.

And the present invention also features the use of at least one compound of formula (I) or of one of its salts in the manufacture of a composition intended to preserve the amount and/or the activity of prostaglandins in the hair follicle.

DETAILED DESCRIPTION OF BEST MODE AND SPECIFIC/PREFERRED EMBODIMENTS OF THE INVENTION

Hereinafter, and unless expressly mentioned, the use of the term "compound of formula (I)" should be understood as meaning both the compound of formula (I) in the neutral, acidic or basic form and in the form of salts.

The term "15-hydroxyprostaglandin dehydrogenase inhibitor" means a compound of formula (I) which is capable of inhibiting or reducing the activity of the enzyme 15-PGDH, in particular of type 1, in human being such as man and/or is capable of inhibiting, reducing or slowing down the reaction catalysed by this enzyme.

According to an advantageous embodiment of the invention, the compound of formula (I) is a specific inhibitor of 15-PGDH; the term "specific inhibitor" means an active principle which should not be or should only to a slight extent be an inhibitor of the synthesis of prostaglandins, in particular of the synthesis of $PGF_{2\alpha}$ or $PGE_2$. According to a specific embodiment of the invention, the inhibitor of 15-PGDH is not or only to a slight extent an inhibitor of the synthesis of prostaglandins, in particular of the synthesis of $PGF_{2\alpha}$ or $PGE_2$. According to a specific embodiment of the invention, the inhibitor of 15-PGDH is not or only to a slight extent an inhibitor of prostaglandin synthase (PGF synthase).

This is because Applicants have now found that PGF synthase is also expressed in the dermal papilla. The maintenance of an effective amount of prostaglandins at the site of action thus results from a complex biological equilibrium between the synthesis and the decomposition of these molecules. The exogenous contribution of compounds which inhibit catabolism will therefore be less effective if this activity is combined with inhibition of the synthesis of these prostaglandins.

The compounds of formula (I), in the salified or nonsalified form, advantageously exhibit an inhibitory activity for 15-PGDH which is greater than the activity inhibiting PGF synthase. In particular, the ratio of the inhibitory activity for PGF synthase to the inhibitory activity for 15-PGDH for a given concentration, which activities are determined in particular by the concentrations which inhibit 50% of the enzymatic activity of PGF synthase ($IC_{50fs}$) and of 15-PGDH ($IC_{50hd}$) respectively, is at least greater than 1 and in particular at least 3:1, advantageously greater than or equal to 5:1. The preferred compounds of the invention exhibit an IC50fs/IC50hd ratio of greater than or equal to 10:1 and in particular of greater than or equal to 15.

"At least one" according to the invention means one or more (2, 3 or more). In particular, the composition can comprise one or more compounds of formula (I). This or these compounds can be cis or trans or Z or E isomers or a mixture of cis/trans or Z/E isomers. They can also be in the tautomeric form. This or these compounds can be enantiomers and/or diastereoisomers or a mixture of these isomers, in particular a racemic mixture.

The term "alkyl radical" means, according to the invention, a hydrocarbonaceous radical which can be saturated or unsaturated and linear or branched. The alkyl radical preferably has from 1 to 10 carbon atoms.

According to the invention, the rings employed for $R_1$, $R_2$, $R_3$, $R_5$, $R_6$, $R_7$, $R_8$, R, R', R", R', $T_1$, $T_2$ and $T_3$ have from 4 to 7 atoms and better still from 5 to 6 atoms. They can be saturated or unsaturated and can optionally contain one or more heteroatoms, such as S, N, O or their combinations. In addition, the rings can contain one or more carbonyl or thiocarbonyl functional groups or both, the carbon of these functional groups forming part of the heterocycle. Mention may be made, as saturated carbonaceous rings which can be used, of the cyclobutyl, cyclopentyl, cyclohexyl or cycloheptyl radical. Mention may be made, as heterocycle Hy, of the pyridine, piperidine, morpholine, pyrrole, furan, thiophene, imidazole, oxazole, thiazole, pyrazole, pyrimidine, piperazine, pyrazine, pyridazine, triazine, pyrrolidine or thiazolidine rings. Mention may be made, as unsaturated carbonaceous rings, of the cyclohexenyl ring and mention may be made, as aryl radicals, of the phenyl or naphthyl radical. In addition, these rings can be substituted, in particular by a substituent $T_2$.

Furthermore, these rings can be alone or fused to another ring with the same or different chemical structure and can thus form condensed rings.

For all the definitions of $R_1$ to $R_8$ and of R, R', R" and R', certain carbons of the saturated or unsaturated carbonaceous rings or heterocycles having 4, 5, 6 or 7 atoms can also form part of a carbonyl or thiocarbonyl functional group, such as, for example:

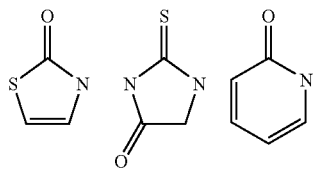

When $R_1$ and $R_2$ form a heterocycle, this heterocycle can, for example, be the pyrrolidine, pyrrole, imidazole, triazole, piperidine, morpholine, piperazine or tetrazole ring.

Mention may be made, as examples of alkyl radical which can be used in the invention, of the methyl, ethyl, isopropyl, n-butyl, tert-butyl, n-hexyl or 2-ethylhexyl radical or the ethylene or propylene radical. This radical can optionally be substituted by one or more substituents $T_4$, for example selected from OR or COOR.

Use may be made, as halogen atom, of the chlorine, fluorine or bromine atom and better still fluorine and chlorine atoms.

According to the invention, the compounds of formula (I) are in the isolated form, that is to say nonpolymeric.

According to one embodiment, at least one of the $R_3$ and $R_4$ groups represents a saturated $C_1$-$C_{20}$ and better still $C_1$-$C_{10}$ alkyl radical, such as, for example, the methyl or ethyl radical, or a heterocycle Hy. For example, at least one of the $R_3$ and $R_4$ groups represents a saturated $C_1$-$C_{20}$ alkyl radical and the other a heterocycle Hy. In particular, $R_3$ represents the methyl or ethyl radical and $R_4$ represents a heterocycle comprising 5 atoms. For example, Hy represents a heterocycle comprising 5 atoms comprising sulfur or oxygen, for example, as heteroatom, such as thiophene or furan.

Advantageously, at least one of the $R_1$ and $R_2$ groups represents a hydrogen atom, a saturated or unsaturated carbonaceous ring and especially an aryl radical. In particular, $R_2$ represents H and $R_1$ represents a phenyl radical optionally substituted by an alkyl or an alkoxy, such as the methoxy group.

The term "salts of compound of formula (I)" means, according to the invention, the organic or inorganic and single or double salts of a compound of formula (I).

Mention may be made, as inorganic salts which can be used according to the invention, of: sodium or potassium salts and salts of zinc ($Zn^{2+}$), of calcium ($Ca^{2+}$), of copper ($Cu^{2+}$), of iron ($Fe^{2+}$), of strontium ($Sr^{2+}$), of magnesium ($Mg^{2+}$), of ammonium and of manganese ($Mn^{2+}$); hydroxides, carbonates, halides, sulfates, nitrates or phosphates.

The organic salts which can be used according to the invention are, for example, triethanolamine, monoethanolamine, diethanolamine, hexadecylamine, N,N,N',N'-tetrakis(2-hydroxypropyl)ethylenediamine or tris(hydroxymethyl)aminomethane salts.

The compounds of formula (I), which may or may not be salified, are known as such and can be prepared in a known manner. For example, the synthesis can be carried out in three stages. The condensation of a ketone with hydroxylamine hydrochloride gives an oxime. The latter can be alkylated by the sodium salt of 2-chloroacetic acid. The acid formed is then converted to an amide via the formation of an acid chloride and reaction of the latter with an amine. Such a preparation is described by A. Buzas et al., *Chimie Thérapeutique*, 1972, 2, 140-142.

No prior art is known to Applicants that discloses or suggests that the 2-alkylideneaminooxyacetamide compounds of formula (I) or their salts have the property of inducing and/or stimulating the growth of human keratinous fibers and in particular of the hair and eyelashes and/or slowing down their loss or that these compounds can be used topically to increase the density of keratinous fibers and more especially that of the hair and eyelashes.

The effective amount of a compound of formula (I) or of one of its salts corresponds to the amount necessary to obtain the desired result (namely, to increase the density of keratinous fibers and in particular of the hair and eyelashes or to promote their growth). One skilled in the art is therefore in a position to evaluate this effective amount, which depends on the nature of the compound used, on the person to which it is applied and on the time of this application.

Hereinafter, unless otherwise indicated, the amounts of the various ingredients of the composition are given as percentage by weight with respect to the total weight of the composition.

To provide an order of magnitude, according to the invention, the compound of formula (I) or one of its salts or a mixture of compounds of formula (I) and/or of their salts can be used in an amount representing from $10^{-3}$% to 10% of the total weight of the composition and preferably in an amount representing from $10^{-3}$% to 5% and better still from $10^{-2}$% to 2% of the total weight of the composition, for example from 0.5 to 2%.

The compositions of the invention can be for cosmetic or pharmaceutical use. Preferably, the compositions of the invention are for cosmetic use. Consequently, the composition should comprise a physiologically acceptable medium which is non-toxic and which is capable of being applied to human skin, including the scalp and eyelids, and to human keratinous fibers. The term "cosmetic" is understood to mean, within the meaning of the invention, a composition with a pleasant appearance, smell and feel.

The compound of formula (I), which may or may not be salified, can be formulated into a composition which has to be ingested, injected or applied to the skin or to keratinous fibers (over any cutaneous region or all of the fibers to be treated).

According to the invention, the compound of formula (I) can be used orally in an amount of 0.1 to 300 mg per day, 5 to 10 mg/d.

A preferred composition of the invention is a composition for cosmetic use and in particular for topical application to the skin and keratinous fibers and more especially to the scalp, hair and eyelashes.

This composition can be provided in any known dosage form suited to the method of use.

For topical application to the skin, the composition can have the form of an aqueous, alcoholic or aqueous/alcoholic solution or suspension or of an oily suspension, of an emulsion with a more or less fluid consistency and in particular a liquid or semi-liquid consistency, obtained by dispersion of a fatty phase in an aqueous phase (O/W) or vice versa (W/O), of an (O/W) or (W/O) solid emulsion, of an aqueous, aqueous/alcoholic or oily gel which is more or less fluid or solid, of a free or compact powder to be used as is or to be incorporated in a physiologically acceptable medium, or also of microcapsules or microparticles, or of vesicular dispersions of ionic and/or nonionic type.

It is also possible to formulate a composition in the form of a foam or in the form of a spray or aerosol then comprising a pressurized propellant.

It can thus be provided in the form of a lotion, serum, milk, O/W or W/O cream, gel, ointment, pomade, powder, balm, patch, impregnated pad, cake or foam.

In particular, the composition for application to the scalp or hair can be provided in the form of a hair care lotion, for example for daily or twice-weekly application, of a shampoo or of a hair conditioner, in particular for twice-weekly or weekly application, of a liquid or solid soap for cleaning the scalp, for daily application, of a product for shaping the hairstyle (lacquer, hairsetting product, styling gel), of a treatment mask, of a cream or of a foaming gel for cleaning the hair. It can also be provided in the form of a hair dye or mascara to be applied with a brush or comb.

Furthermore, for application to the eyelashes or body hairs, the composition to which the invention relates can be provided in the form of a pigmented or nonpigmented mascara, to be applied with a brush to the eyelashes or alternatively to the beard or moustache hairs.

For a composition for administration by injection, the composition can be provided in the form of an aqueous lotion or of an oily suspension. For administration by the oral route, the composition can be provided in the form of capsules, of granules, of syrups to be taken orally or of tablets.

According to a specific embodiment, the composition according to the invention is provided in the form of a hair cream or lotion, of a shampoo, of a hair conditioner, of a hair mascara or of a mascara for the eyelashes.

The amounts of the various constituents of the physiological medium of the composition according to the invention are those generally used in the fields under consideration. In addition, these compositions are prepared according to conventional methods.

When the composition is an emulsion, the proportion of the fatty phase can range from 2% to 80% by weight and preferably from 5% to 50% by weight with respect to the total weight of the composition. The aqueous phase is adjusted according to the content of fatty phase and of compound(s) (I) and according to the content of possible additional ingredients, in order to obtain 100% by weight. In practice, the aqueous phase represents from 5% to 99.9% by weight.

The fatty phase can comprise fatty or oily compounds which are liquid at ambient temperature (25° C.) and atmospheric pressure (760 mmHg), generally known as oils. These oils may or may not be compatible with one another and may form a macroscopically homogeneous liquid fatty phase or a two- or three-phase system.

The fatty phase can, in addition to the oils, comprise waxes, gums, lipophilic polymers, or "pasty" or viscous products comprising solid parts and liquid parts.

The aqueous phase comprises water and optionally an ingredient miscible in any proportion with water, such as lower $C_1$ to $C_8$ alcohols, for example ethanol or isopropanol, polyols, such as propylene glycol, glycerol or sorbitol, or else acetone or ether.

The emulsifiers and coemulsifiers used to produce a composition in the form of an emulsion are those generally used in the cosmetic and pharmaceutical fields. In addition, their nature depends on the sense of the emulsion. In practice, the emulsifier and optionally the coemulsifier are present in the composition in a proportion ranging from 0.1% to 30% by weight, preferably from 0.5 to 20% by weight and better still from 1 to 8%. In addition, the emulsion can comprise lipid vesicles and in particular liposomes.

When the composition is in the form of an oily solution or gel, the fatty phase can represent more than 90% of the total weight of the composition.

Advantageously, the composition is an aqueous, alcoholic or aqueous/alcoholic solution or suspension and better still a water/ethanol solution or suspension. The alcohol fraction can represent from 5% to 99.9% and better still from 8% to 80%.

For a mascara application, in particular for the eyelashes, the composition of the invention is a wax-in-water or wax-in-oil dispersion, a gelled oil or an aqueous gel, this mascara being, furthermore, with or without pigment.

The compositions of the invention can comprise, in addition, other ingredients generally used in the fields concerned selected from solvents, thickeners or gelling agents for the aqueous phase or for the oily phase, coloring materials which are soluble in the medium of the composition, solid particles of the filler or pigment type, antioxidants, preservatives, fragrances, electrolytes, neutralizing agents, film-forming polymers, UV blocking agents, such as sunscreens, cosmetic and pharmaceutical active principles, or their mixtures. These additives can be present in the composition according to the amounts generally used in the cosmetic and dermatological field and in particular in a proportion of 0.01 to 50% of the total weight of the composition and better still of 0.1 to 20% and, for example, of 0.1 to 10%. These additives, depending on their nature, can be introduced into the fatty phase, into the aqueous phase and/or into the lipid vesicles and in particular into liposomes.

Of course, one skilled in the art will take care to choose the possible additional additives and/or their amounts so that the advantageous properties of the composition according to the invention, namely the specific inhibition of type 1 15-PGDH in particular or the increase in the density of keratinous fibers (hair or eyelashes), are not, or not substantially, detrimentally affected by the envisaged addition.

Mention may be made, as solvents which can be used in the invention, of lower $C_2$ to $C_8$ alcohols, such as ethanol or isopropanol, propylene glycol and certain light cosmetic oils, such as $C_6$ to $C_{16}$ alkanes.

Mention may be made, as oils which can be used in the invention, of oils of mineral origin (liquid petrolatum, hydrogenated isoparaffin), oils of vegetable origin (liquid fraction of karite butter, sunflower oil, apricot oil, fatty alcohol or fatty acid), oils of animal origin (perhydrosqualene), synthetic oils (fatty acid esters, purcellin oil), silicone oils (phenyltrimethicone, linear or cyclic polydimethylsiloxane) and fluorinated oils (perfluoropolyethers). Mention may be made, as waxes, of silicone waxes, beeswax, rice wax, candelilla wax, carnauba wax, paraffin wax or polyethylene wax.

Mention may be made, as emulsifiers which can be used in the invention, of, for example, glyceryl stearate or laurate, sorbitol stearates or oleates, alkyl dimethicone copolyols (with alkyl ≧8) and their mixtures for a W/O emulsion. Use may also be made of polyethylene glycol monostearate or monolaurate, polyoxyethylenated sorbitol stearate or oleate, dimethicone copolyols and their mixtures for an O/W emulsion.

Mention may be made, as hydrophilic gelling agents which can be used in the invention, of carboxyvinyl polymers (carbomer), acrylic copolymers, such as acrylate/alkyl acrylate copolymers, polyacrylamides, polysaccharides, such as hydroxypropylcellulose, natural gums and clays and mention may be made, as lipophilic gelling agents, of modified clays, such as bentones, metal salts of fatty acids, such as aluminum stearates, hydrophobic treated silica, ethylcellulose or their mixtures.

The compositions can additionally comprise a cosmetic or pharmaceutical active principle other than the compounds of formula (I) which can be hydrophilic and is selected from proteins or protein hydrolysates, amino acids, polyols, urea, allantoin, sugars and sugar derivatives, water-soluble vitamins, plant extracts (those of Iridaceae or of soya) and hydroxy acids, such as fruit acids or salicylic acid; or lipophilic and is selected from retinol (vitamin A) and its derivatives, in particular ester (retinol palmitate), tocopherol (vitamin E) and its derivatives, in particular ester (tocopherol acetate), essential fatty acids, ceramides, essential oils, salicylic acid derivatives, such as 5-(n-octanoyl)salicylic acid, esters of hydroxy acids, phospholipids, such as lecithin, or their mixtures.

According to a specific embodiment of the invention, the compound of formula (I) or one of its salts can be combined with additional active compounds which promote the regrowth and/or which limit the loss of keratinous fibers (hair, eyelashes). These additional compounds are selected in particular from lipoxygenase inhibitors, such as disclosed in EP-0,648,488, bradykinin inhibitors, disclosed in particular in EP-0,845,700, prostaglandins and their derivatives, in particular those disclosed in WO 98/33497, WO 95/11003, JP 97-100091 or JP 96-134242, prostaglandin receptor agonists or antagonists, nonprostanoic prostaglandin analogues, such as disclosed in EP-1,175,891 and EP-1,175,890, WO 01/74307, WO 01/74313, WO 01/74314, WO 01/74315 or WO 01/72268, or their mixtures.

Mention may be made, as other additional active compounds which promote the growth of keratinous fibers (of the hair) which can be present in the composition according to the invention, of vasodilators, anti-androgens, cyclosporins and their analogues, anti-microbials and anti-fungals, anti-inflammatories or retinoids, alone or as a mixture.

The vasodilators which can be used are in particular potassium channel agonists, including minoxidil and also the compounds disclosed in U.S. Pat. Nos. 3,382,247, 5,756,092, 5,772,990, 5,760,043, 5,466,694, 5,438,058 or 4,973,474, cromakalim, nicorandil and diazoxide, alone or in combination.

The anti-androgens which can be used include in particular steroidal or nonsteroidal inhibitors of 5α-reductase, such as finasteride and the compounds disclosed in U.S. Pat. No. 5,516,779, cyprosterone acetate, azelaic acid, its salts and its derivatives and the compounds disclosed in U.S. Pat. No. 5,480,913, flutamide, oxendolone, spironolactone, diethylstilbestrol and the compounds disclosed in U.S. Pat. Nos. 5,411,981, 5,565,467 and 4,910,226.

The anti-microbial or anti-fungal compounds can be selected from selenium derivatives, octopirox, triclocarban, triclosan, zinc pyrithione, itraconazole, asiatic acid, hinokitiol, mupirocin, tetracyclines, in particular erythromycin and the compounds disclosed in EP-0,680,745, clindamycin hydrochloride, benzoyl peroxide or benzyl peroxide, minocyclin and the compounds belonging to the class of the imidazoles, such as econazole, ketoconazole or miconazole or their salts, or nicotinic acid esters, including in particular tocopherol nicotinate, benzyl nicotinate and $C_1$-$C_6$ alkyl nicotinates, such as methyl nicotinate or hexyl nicotinate.

The anti-inflammatories can be selected from steroidal anti-inflammatories, such as glucocorticoids or corticosteroids (for example: hydrocortisone), and nonsteroidal anti-inflammatories, such as glycyrrhetinic acid and α-bisabolol, benzydamine, salicylic acid and the compounds disclosed in EP-0,770,399, WO 94/06434 and FR-2,268,523.

The retinoids can be selected from isotretinoin, acitretin and tazarotene.

Mention may be made, as other active compounds for promoting the growth and/or limiting the loss of keratinous fibers (hair, eyelashes) which can be used in combinations with the compound of formula (I), of aminexil, 6-O-[(9Z,12Z)-octadeca-9,12-dienoyl]hexapyranose, benzalkonium chloride, benzethonium chloride, phenol, oestradiol, chlorpheniramine maleate, chlorophyllin derivatives, cholesterol, cysteine, methionine, menthol, peppermint oil, calcium pantothenate, panthenol, resorcinol, protein kinase C activators, glycosidase inhibitors, glycosaminoglycanase inhibitors, pyroglutamic acid esters, hexosaccharidic acid or acylhexosaccharic acid, aryl-substituted ethylenes, N-acylated amino acids, flavonoids, ascomycin derivatives and analogues, histamine antagonists, saponins, proteoglycanase inhibitors, oestrogen agonists and antagonists, pseudopterins, cytokines and growth factor promoters, IL-1 or IL-6 inhibitors, IL-10 promoters, TNF inhibitors, benzophenones, hydantoin, retinoic acid; vitamins, such as vitamin D, analogues of vitamin B12 and pantothenol; triterpenes, such as ursolic acid and the compounds disclosed in U.S. Pat. Nos. 5,529,769, 5,468,888 or 5,631,282; anti-pruritic agents, such as thenaldine, trimeprazine or cyproheptadine; agents for combating parasites, in particular metronidazole, crotamiton or pyrethroids; calcium antagonist agents, such as cinnarizine, diltiazem, nimodipine, verapamil, alverine and nifedipine; hormones, such as oestriol or its analogues, thyroxine and its salts, or progesterone; FP receptor (receptor to prostaglandins of the F type) agonists, such as latanoprost, bimatroprost, travoprost or unoprostone; their mixtures.

Advantageously, the compositions according to the invention comprise at least one type 1 15-PGDH inhibitor as defined above and at least one prostaglandin or one prostaglandin derivative, such as, for example, prostaglandins of the 2 series, including in particular $PGF_{2\alpha}$ and $PGE_2$, in the salt or ester form (example, the isopropyl esters), their derivatives, such as 16,16-dimethyl-$PGE_2$, 17-phenyl-$PGE_2$, 16,16-dimethyl-$PGF_{2\alpha}$ or 17-phenyl-$PGF_{2\alpha}$, or prostaglandins of the 1 series, such as 1 1-deoxyprostaglandin $E_1$ or 1-deoxyprostaglandin $E_1$, in the salt or ester form, their analogues, in particular latanoprost, travoprost, bimatoprost, fluprostenol, cloprostenol, viprostol, butaprost, misoprostol or unoprostone, their salts or their esters.

Advantageously, the compositions comprise at least one nonprostanoic agonist of the EP2 and/or EP4 receptors, in particular as disclosed in EP-1,175,892.

It is also possible to employ the composition comprising at least the compound of formula (I), which may or may not be salified, in the liposomed form, such as disclosed in particular in WO 94/22468. Thus, the compound encapsulated in the liposomes can be delivered selectively to the hair follicle or the base of the eyelash.

The compositions according to the invention can be applied to the areas of the scalp and hair of an individual which are suffering from alopecia and can optionally be left in contact for several hours and can optionally be rinsed.

It is possible, for example, to apply the composition comprising an effective amount of a compound of formula (I), which may or may not be salified, in the evening, to keep this composition in contact with the fibers overnight and optionally to shampoo in the morning. These applications can be repeated daily for one or more months, depending on the individual.

Advantageously, in the process according to the invention, between 5 and 500 µl of a solution or composition as defined above, comprising from 0.001% to 5% of 15-PGDH inhibitor, are applied to the areas of the scalp to be treated.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

Implementational examples of the invention will now be given by way of illustration.

Mention may be made, as examples of 2-alkylideneaminooxyacetamide compounds of formula (I) which can be used in the invention, of the following compounds:

Compound 1: N-Phenyl-2-({[(1Z)-1-(thien-2-yl)-ethylidene]amino}oxy)acetamide:

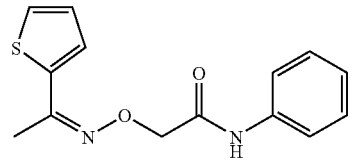

Compound 2: 2-({[(1Z)-1-(2-Furyl)ethylidene]amino}oxy)-N-phenylacetamide:

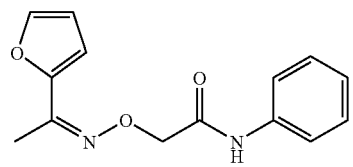

Compound 3: N-(4-Methoxyphenyl)-2-({[(1Z)-1-(thien-2-yl)ethylidene]amino}oxy)acetamide:

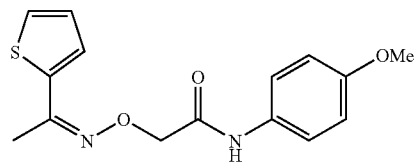

Compound 4: N-Phenyl-2-({[(1Z)-1-(thien-2-yl)propylidene]amino)oxy)acetamide:

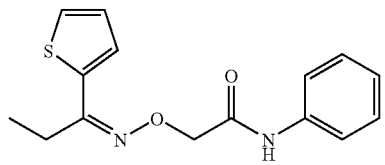

Compound 5: 2-{[(1-Methylethylidene)amino]oxy}-N-phenylacetamide:

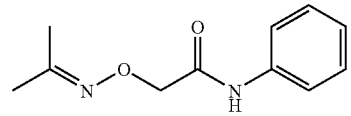

Compound 6: N-Methyl-2-({[(1Z)-1-(thien-2-yl)-ethylidene]amino}oxy)acetamide:

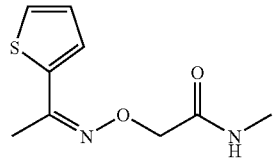

Compound 7: N-Methyl-N-phenyl-2-({[(1Z)-1-(thien-2-yl)ethylidene]amino}oxy)acetamide:

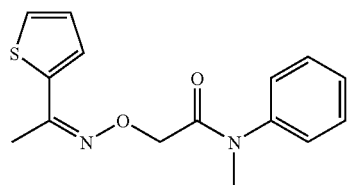

Compound 8: N-(2-Hydroxyethyl)-N-phenyl-2-({[(1Z)-1-(thien-2-yl)ethylidene]amino}oxy)acetamide:

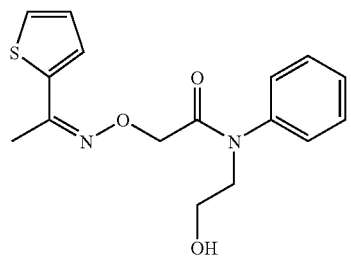

Examples of the synthesis of compounds to which the invention relates are given below.

Synthesis provided:

The compounds of formula (I) can be prepared by synthetic methods known in the literature. For example, the synthesis can be carried out in three stages. The condensation of a ketone with hydroxylamine hydrochloride gives an oxime. The latter can be alkylated by the sodium salt of 2-chloroacetic acid. The acid formed is then converted to an amide via the formation of an acid chloride and reaction of the latter with an amine. Such a preparation is described by A. Buzas et al., *Chimie Thérapeutique*, 1972, 2, 140-142.

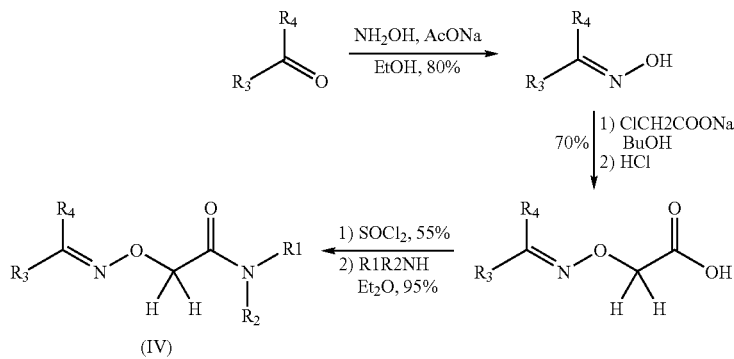

(IV)

Example 1

Preparation of 2-{[(1-methylethylidene)amino]oxy}-N-phenylacetamide in 3 Stages—Compound 5

Stage 1: Synthesis of Acetone Oxime

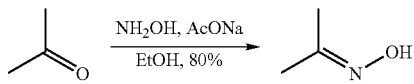

5.8 g of acetone, 10.4 g of hydroxylamine hydrochloride and 19.1 g of sodium carbonate are placed in 150 ml of 60% EtOH. The reaction medium is heated at reflux for 12 h. After cooling, the ethanol is distilled off and then the product is extracted with ethyl acetate. This phase is dried over sodium sulfate and the solvent is evaporated to give the acetone oxime.

Stage 2: Synthesis of {[(1-methylethylidene)amino]oxy}acetic acid

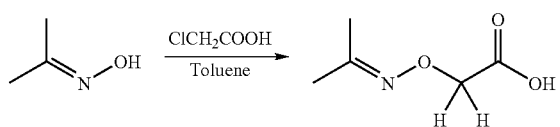

7.3 g of acetone oxime, 14.2 g of chloroacetic acid and 2% of tetrabutylammonium bromide are placed in 80 ml of toluene. An aqueous sodium hydroxide solution (10 g of sodium hydroxide dissolved in 150 ml of water) is added dropwise. The reaction medium is stirred for 1 h and then the toluene is evaporated under vacuum. The residue is then acidified with concentrated hydrochloric acid to pH 2.5, then washed with water and extracted twice with ethyl acetate. The organic phase is dried over sodium sulfate and the solvent is evaporated to give the expected product.

Stage 3: Synthesis of 2-{[(1-methylethylidene)amino]oxy}-N-phenylacetamide

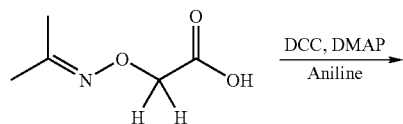

-continued

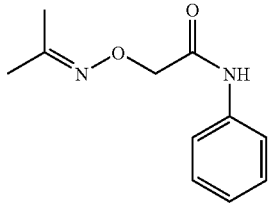

1.21 g of the oxime prepared previously and 0.85 g of aniline are placed in 10 ml of dichloromethane. 1.12 g of 4-dimethylaminopyridine and 2.05 g of N,N'-dicyclohexylcarbodiimide are then added. The reaction medium is then stirred for 16 h. After washing with water, the product is extracted with ethyl acetate. The organic phase is dried over sodium sulfate and the solvent is evaporated. The product is then recrystallized from an ethyl acetate/petroleum ether mixture.

Example 2

Demonstration of the Specific Inhibitory Properties with Respect to 15-PGDH of the Compounds of Formula (I)

1) Test on type 1 15-PGDH:

The enzyme type 1 15-PGDH is obtained as disclosed in Application FR 02/05067, assigned to the assignee hereof, in suspension in a suitable medium at a concentration of 0.3 mg/ml, then blocked at −80° C. For the requirements of the test, this suspension is defrosted and stored in ice.

Furthermore, a Tris 100 mM, pH=7.4, buffer comprising 0.1 mM of dithiothreitol (D5545, Sigma-Aldrich, L'isle D'Abeau Chesne, BP 701, 38297, Saint Quentin Fallavier), 1.5 mM of β-NAD (N6522, Sigma-Aldrich, L'isle D'Abeau Chesne, BP 701, 38297, Saint Quentin Fallavier) and 50 μM of prostaglandin $E_2$ (P4172, Sigma-Aldrich, L'isle D'Abeau Chesne, BP 701, 38297, Saint Quentin Fallavier) is prepared.

0.965 ml of this buffer (brought beforehand to 37° C.) is introduced into the cell of a spectrophotometer (Perkin-Elmer, Lambda 2) thermostatically controlled at 37° C., the wavelength of which for the measurement is adjusted to 340 nm. 0.035 ml of enzymatic suspension at 37° C. is introduced into the cell concomitantly with the recording (corresponding to an increase in optical density at 340 nm). The maximum rate of reaction is noted.

The test values (comprising the compounds (I)) are compared with the control value (without compound (I)); the results indicated represent the concentration at which the compound of formula (I) reduces the enzymatic activity of 15-PGDH by 50%, namely $IC_{50dh}$.

2) Test on PGF Synthase:

The enzyme PGFS is obtained as disclosed in FR-A-02/05067, at a concentration of 0.5 mg/ml, in suspension in an appropriate medium, and is blocked at −80° C. For the requirements of the test, this suspension is defrosted and stored in ice.

Furthermore, a Tris 100 mM, pH=6.5, buffer comprising 20 µM of 9,10-phenanthrenequinone*(P2896, Sigma-Aldrich, L'isle D'Abeau Chesne, BP 701, 38297, Saint Quentin Fallavier) and 100 µM of β-NADPH (N1630, Sigma-Aldrich, L'isle D'Abeau Chesne, BP 701, 38297, Saint Quentin Fallavier) is prepared in a brown bottle (exclusion of light). *A mother solution assaying 1 mM is prepared in absolute ethanol and is brought to 40° C.; the bottle is placed in an ultrasonic bath to facilitate the dissolution of the product.

0.950 ml of this buffer (brought beforehand to 37° C.) is introduced into the cell of a spectrophotometer (Perkin-Elmer, Lambda 2) thermostatically controlled at 37° C., the wavelength of which for the measurement is adjusted to 340 nm. 0.05 ml of enzymatic suspension at 37° C. is introduced into the cell concomitantly with the recording (corresponding to a fall in optical density at 340 nm). The maximum rate of reaction is noted.

The test values (comprising the compound (I)) are compared with the control value (without compound (I)); the results indicated represent the concentration at which the compound of formula (I) reduces the enzymatic activity of PGFS by 50%, namely $IC_{50fs}$.

| Compound | Structure | $IC_{50}$ (µM) 15-PGDH | PGFS |
|---|---|---|---|
| 1 | (structure shown) | 6 | 50 to 100 |

From this table, it will be seen that Compound 1 is indeed a type 1 15-PGDH inhibitor. Moreover, it inhibits 15-PGDH more effectively than PGFS. Thus, the ratio $IC_{50fs}/IC_{50dh}$ is between 8.3 and 16.7.

The compositions below are obtained by the usual techniques commonly used in the cosmetic or pharmaceutical field.

Example 3

Hair Lotion

| | |
|---|---|
| Compound 1 | 1.00 g |
| Propylene glycol | 30.00 g |
| Ethyl alcohol | 40.00 g |
| Water q.s. for | 100.00 g |

This lotion is applied to the scalp one or two times daily at the rate of 1 ml per application, the scalp being lightly massaged to bring about the penetration of the active principle. The hair is subsequently dried in the open air. This lotion makes it possible to reduce hair loss and to promote hair regrowth.

Example 4

Hair Lotion

| | |
|---|---|
| Compound 1 | 0.10 g |
| Latanoprost | 0.10 g |
| Propylene glycol | 30.00 g |
| Ethyl alcohol | 40.00 g |
| Water q.s. for | 100.00 g |

Example 5

Wax/Water Mascara

| | |
|---|---|
| Beeswax | 6.00% |
| Paraffin wax | 13.00% |
| Hydrogenated jojoba oil | 2.00% |
| Water-soluble film-forming polymer | 3.00% |
| Triethanolamine stearate | 8.00% |
| Compound 1 | 1.00% |
| Black pigment | 5.00% |
| Preservative q.s. | |
| Water q.s. for | 100.00% |

The mascara is applied to the eyelashes like a conventional mascara with a mascara brush.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A regime or regimen for inducing and/or stimulating the growth of keratinous fibers and/or slowing the loss and/or increasing the density thereof, comprising administering to a mammalian subject in need of such treatment, for such period of time as required to elicit the desired effect, a thus effective amount of a compound having one of the following fomulae:

-continued

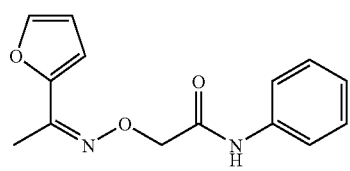

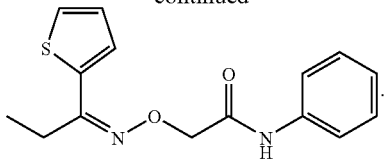

2. A regime or regimen for inhibiting type 1 human 15-hydroxyprostaglandin dehydrogenase, comprising administering to a mammalian subject in need of such treatment, for such period of time as required to elicit the desired effect, a thus effective amount of a compound as defined in claim 1.

3. The regime or regimen as defined by claim 1, comprising topically applying said compound onto the keratinous fibers of said mammalian subject.

4. The regime or regimen defined by claim 1, said keratinous fibers comprising human hair, eyebrows, eyelashes, beard hairs, moustache hairs and/or pubic hairs.

* * * * *